United States Patent [19]

Nehring

[11] Patent Number: 4,681,571
[45] Date of Patent: Jul. 21, 1987

[54] SUCTION CANISTER WITH DISPOSABLE LINER AND CHECK VALVE

[75] Inventor: John R. Nehring, East Greenwich, R.I.

[73] Assignee: C. R. Bard, Inc., Murray Hill, N.J.

[21] Appl. No.: 256,711

[22] Filed: Apr. 23, 1981

[51] Int. Cl.⁴ .............................................. A61M 1/00
[52] U.S. Cl. ...................................... 604/320; 137/205
[58] Field of Search ............................... 137/202, 205; 128/276–278, 760, DIG. 21, 766, 767; 604/307, 319, 320, 323, 324, 325, 326

[56] References Cited

U.S. PATENT DOCUMENTS

| | | | |
|---|---|---|---|
| Re. 25,939 | 12/1965 | Krammes | 15/320 |
| 2,597,715 | 5/1952 | Erikson | 128/272 |
| 2,778,448 | 1/1957 | Graves | 183/43 |
| 2,999,500 | 9/1961 | Schurer | 128/276 |
| 3,032,037 | 5/1962 | Huber | 128/276 |
| 3,191,600 | 6/1965 | Everett | 604/319 |
| 3,466,671 | 9/1969 | Siposs | 128/DIG. 21 |
| 3,556,101 | 1/1971 | Economou | 128/277 |
| 3,680,560 | 8/1972 | Pannier, Jr. et al. | 128/276 |
| 3,685,517 | 8/1972 | Reynolds et al. | 128/277 |
| 3,704,709 | 12/1972 | Sorenson et al. | 128/277 |
| 3,719,197 | 3/1973 | Pannier, Jr. et al. | 137/205 |
| 3,745,999 | 7/1973 | Deaton | 128/277 |
| 3,768,478 | 10/1973 | Fertik et al. | 128/276 |
| 3,773,091 | 11/1973 | Boyd et al. | 137/205 |
| 3,780,738 | 12/1973 | Deaton | 128/277 |
| 3,814,098 | 6/1974 | Deaton | 128/276 |
| 3,848,628 | 11/1974 | Deaton et al. | 137/434 |
| 4,022,209 | 5/1977 | Nehring | 128/278 |
| 4,111,204 | 9/1978 | Hessel | 128/276 |
| 4,228,798 | 10/1980 | Deaton | 128/276 |
| 4,275,732 | 6/1981 | Gereg | 128/276 |
| 4,278,089 | 7/1981 | Huck et al. | 128/278 |

FOREIGN PATENT DOCUMENTS

| | | |
|---|---|---|
| 542410 | 1/1932 | Fed. Rep. of Germany . |
| 2039745 | 8/1980 | United Kingdom ............... 128/278 |

OTHER PUBLICATIONS

"The CRO System", Medi-Vac Corp. Abilene, Texas 79604, 1980.
Aortic Valve Prothesis, "The Bulletin", Dow Corning Corp., Midland, Mich., Oct. 1959, vol. 1, No. 1.

*Primary Examiner*—C. Fred Rosenbaum
*Assistant Examiner*—J. L. Kruter
*Attorney, Agent, or Firm*—Charles B. Smith

[57] ABSTRACT

A medical fluid suction canister and method of use are disclosed. Suction is drawn on a liner within the canister through a check valve, preferably a duckbill check valve and, as a result, fluid from a patient flows into the liner. The check valve prevents the reverse flow of air into the liner should there be an operating upset and ensures that the liner remains fully expanded.

7 Claims, 28 Drawing Figures

SUCTION CANISTER WITH DISPOSABLE LINER AND CHECK VALVE

BACKGROUND OF THE INVENTION

This invention relates to the field of medical fluid collection devices for receiving fluids from patients and particularly to those devices having removable and/or disposable liners (line-in-canister devices). Medical fluid collection devices are used for suctioning wounds or abscesses or during surgery areas filling with blood or other fluids or for the collection of blood from donors.

There are three types of liner-in-canister suction devices. One, devices in which there is no communication between the inside of the liner and the void space between the outside of the liner and the inside of the canister housing. In these devices vacuum drawn on the void space (as by a hospital's vacuum system) causes the liner to expand. The resulting reduced pressure in the liner draws the fluid to be suctioned into the liner. Neither air nor liquid pulled into the liner will enter the void space or the hospital's vacuum system unless the liner fails. See, e.g., U.S. Pat. Nos. 2,597,715, 2,999,500, and 3,032,037.

Two, devices in which there is extensive communication between the liner and the void space so that the pressure is the same in both (excluding hydrostatic pressure of any liquid in the liner). With this type of unit, air is constantly drawn out of the liner when vacuum is applied and unless an internal safety device is provided, liquid can easily overflow the liner into the void space and may be drawn into the hospital's vacuum system. See, e.g., U.S. Pat. No. 3,704,709.

Three, suction devices in which there is limited communication between the void space and the liner. These devices have small openings in the liner and in some cases the openings have flow retarders to make the pressure in the liner higher than that in the void only when vacuum is first applied so that the liner will expand, after which the pressures equalize. See. e.g., U.S. Pat. Nos. 3,556,101, 3,680,560, and 3,848,628.

A problem with the devices of the first type (no communication) is that if air is sucked into the liner (as when used with an open wound), it cannot escape. A problem with the devices of the second and third types (full- and limited-communication, respectively) is that air normally contacts the fluid collected in the liner and, thus, aseptic and/or air-free collection of fluid is impossible. A further problem with some of the devices of the third type (e.g., U.S. Pat. No. 3,680,560) is that certain operating upsets (for instance, blockage of the patient or vacuum source tube) tend to make the liner collapse. Such collapse makes it difficult to tell how much liquid has been suctioned into the liner because the walls of the liner are not in their normal position adjacent the walls of the canister, which often has volumetric markings.

SUMMARY OF THE INVENTION

An invention has now been developed which overcomes these problems and provides the additional benefits noted below. Broadly, the apparatus of this invention is a medical suction canister for receiving fluid from a patient under the force of vacuum, said canister comprising:

(a) a housing;
(b) a liner disposed within the housing;
(c) a fluid path for conducting the fluid from the patient to the inside of the liner;
(d) a first vacuum path for applying suction to the inside of the liner to remove gas therefrom; and
(e) a check valve in the vacuum path that permits gas to leave the liner but blocks the return flow of gas through the vacuum path to the liner.

In a preferred embodiment, the canister comprises:
(a) a housing with a removable top;
(b) a liner disposed within the housing hermetically attached to the removable top, a void space being formed between the outside of the liner and the inside of the housing;
(c) an inlet in the top for conducting the fluid from the patient to the inside of the liner;
(d) a vacuum outlet in the top for conducting gas from the inside of the liner to the source of vacuum, said top having (i) a float valve to prevent liquid flow through the outlet when the liquid level in the liner reaches a predetermined height and (ii) a duckbill check valve to allow gas to leave the liner through the outlet but to prevent the reverse flow of gas through the outlet if gas attempts to reenter the liner; and
(e) a vacuum flow path connecting the vacuum outlet with the void space between the outside of the liner and the inside of the housing.

The process of this invention for suctioning medical fluids from a patient utilizes the foregoing apparatus and comprises:
(a) fluidly connecting the patient to the fluid path of the canister; and
(b) fluidly connecting a source of vacuum to the first vacuum path.

The apparatus of the present invention provides many benefits as compared to the prior art devices. With the new device the pressure in the liner is always greater than that in the void space, not only during initial application of the vacuum to the device. Accordingly, the liner expands when vacuum is first applied but does not collapse if the vacuum source tube should be blocked accidentally. Because air cannot flow from the void space into the liner, aseptic collection of fluid is possible. If air is sucked into the liner, it is withdrawn through the check valve in the vaccum path. The device is inexpensive enough to be disposable but only the lid and attached liner need be discarded in some embodiments since the container portion may be reused with a fresh lid and liner.

BRIEF DESCRIPTION OF THE DRAWINGS

To facilitate further description of the invention, the following drawings are provided in which.

DETAILED DESCRIPTION OF THE INVENTION

Figures 1, 2, 3:
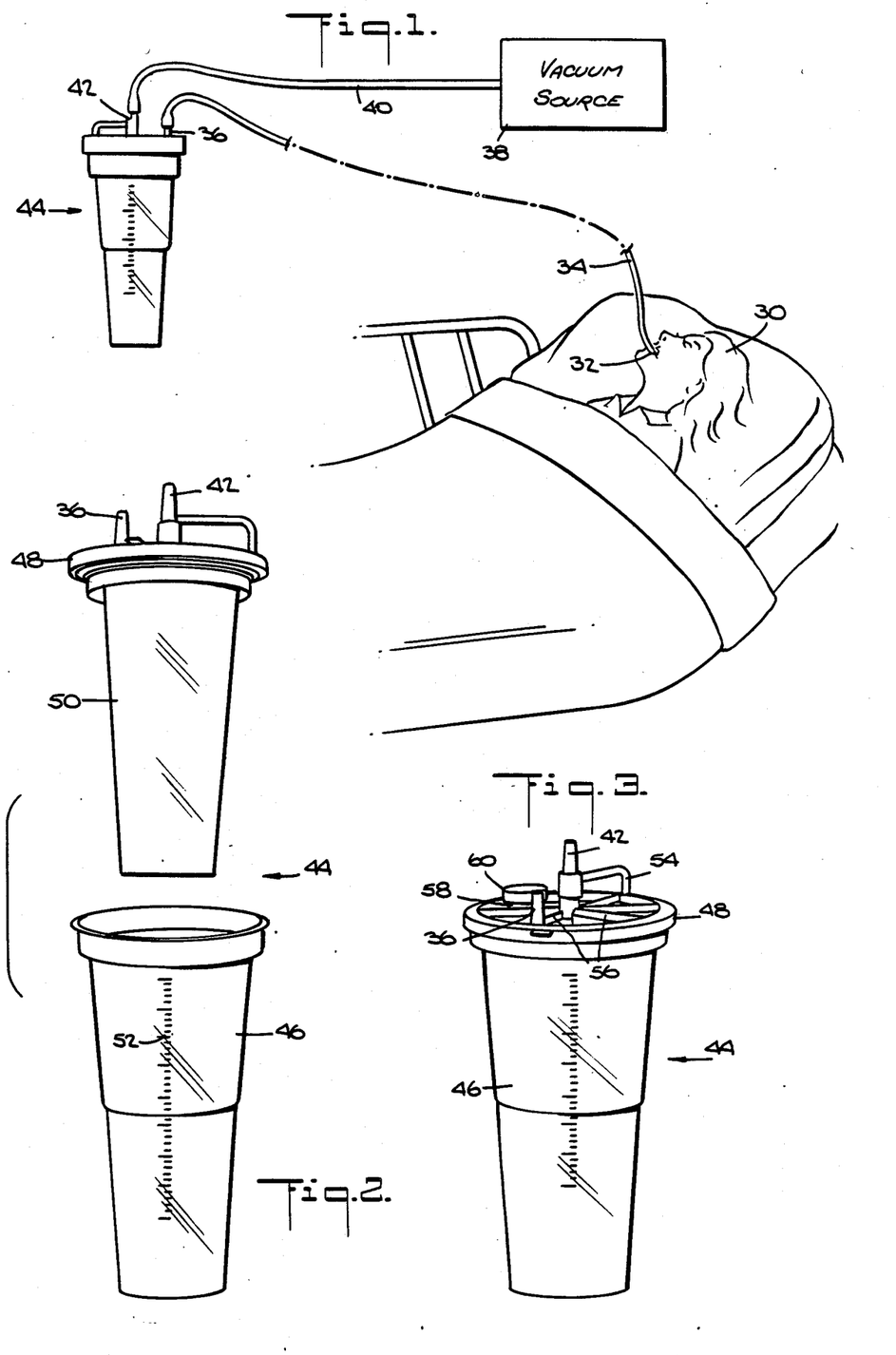
FIG. 1 shows one embodiment of the present invention used to suction fluid from a medical patient.
FIG. 2 is an exploded view of the device showing the liner attached to the canister top.
FIG. 3 is a perspective view of the assembled device.

FIG. 1 shows one embodiment of the invention, suction canister 44, used to suction fluid through tube 34 from hositial patient 30 at drainage site 32. Vacuum source 38 draws suction on canister 44 through tube 40, which is attached to the canister at vacuum connection 42. Tubing 34 is attached to the canister at fluid connection 36.

FIG. 2 is an exploded view of canister 44. The housing comprises top or lid 48 and container 46, having volumetric indicia 52. Liner 50 is hermetically attached to and depends from top 48.

FIG. 3 is another view of the assembled unit. Lid 48 has reinforcing ribs 56 and pour spout 58 with cap 60. Vacuum piping 54 (described in further detail below) connects vacuum connection 42 with vacuum connection 62 (FIG. 4).

Figure 4:
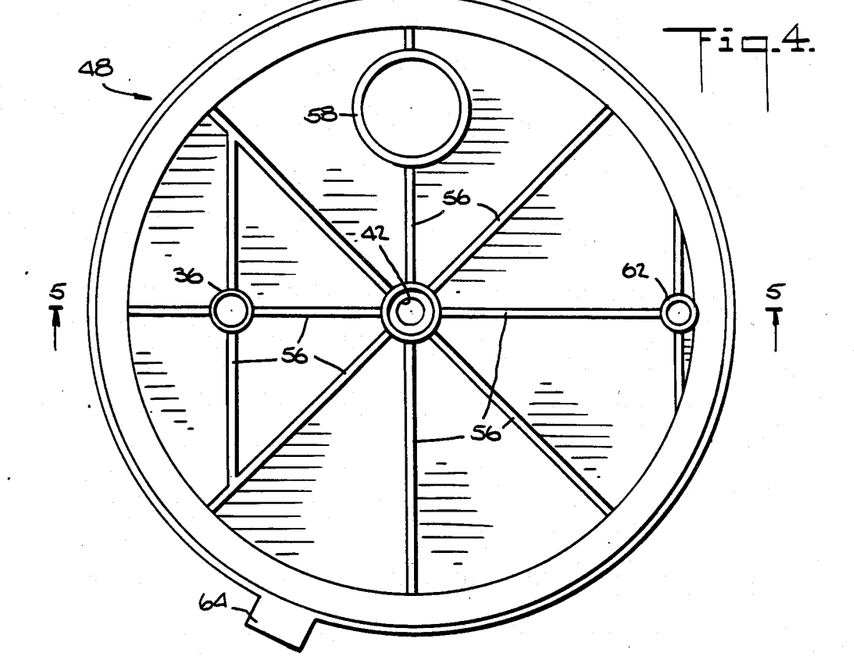
FIG. 4 is a top view of the device.

FIG. 4 is a plan view of top 48. In this view, piping 54 (shown in FIG. 3), which connects vacuum connections 42 and 62, is not visible. Pour spout 58 is shown without its cap 60, and the pattern of reinforcing ribs 56 is seen.

Figure 5:
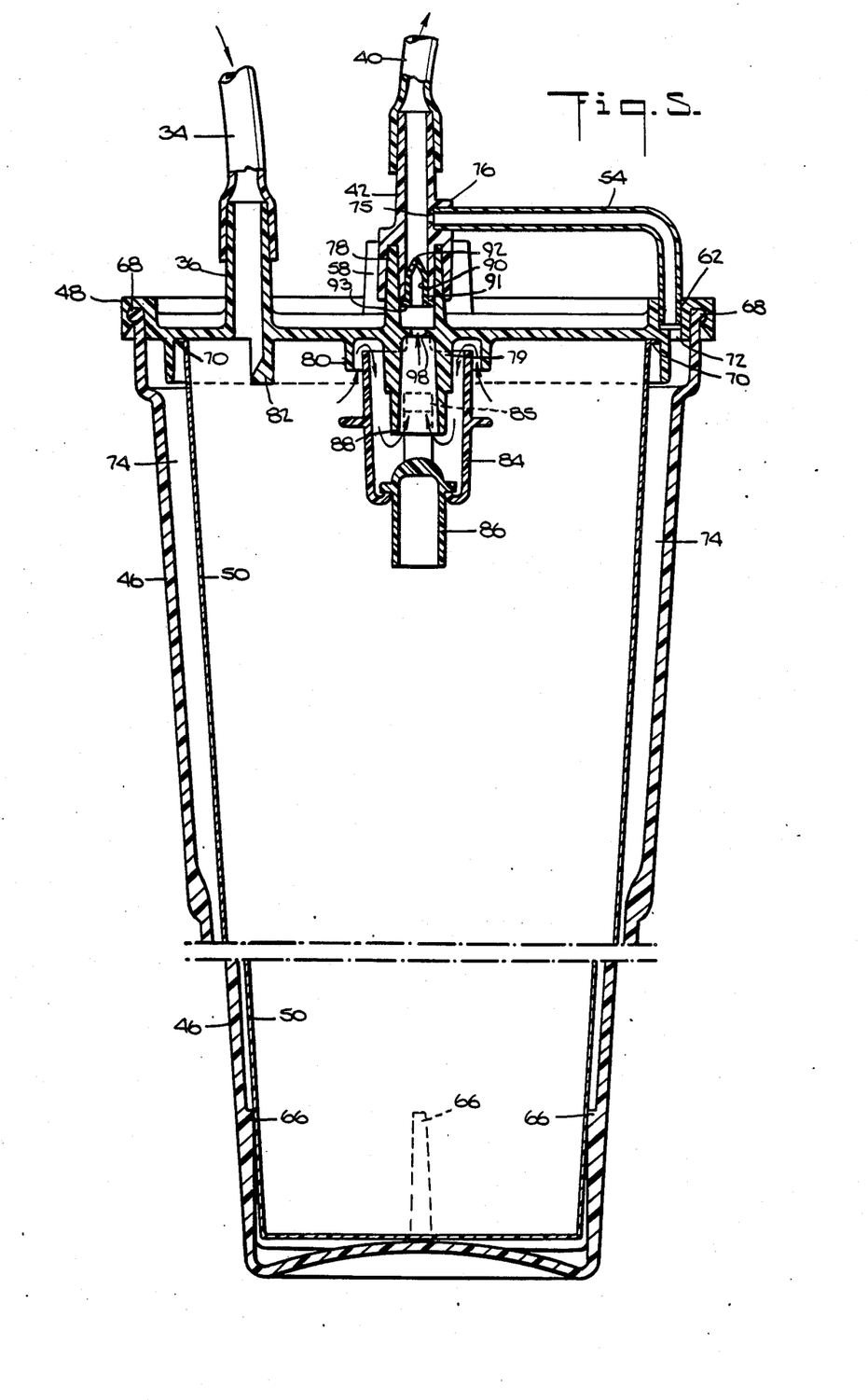
FIG. 5 is an enlarged sectional elevational view of the device taken along line 5—5 of FIG. 4.

FIG. 5 is a cross-sectional view of the device taken along line 5—5 of FIG. 4. Lid 48 snap-fits onto upper rim 68 of the sidewall of container 46. Upper circumferential rim 70 of flexible liner 50 is heat-sealed to the underside of lid 48 so that no fluid can pass in or out of the liner through the seal. Liner 50 when fully expanded fills container 46 in the manner shown, with the bottom walls of the liner resting against four support ribs 66 (only three of which are shown). The ribs facilitate removal of liquid-filled liners from the container.

Void space 74 lies between the outside of liner 50 and the inside of container 46. When lied 48 is firmly seated on rim 68, the only fluid communication to void space 74 is through opening 72 of vacuum connection 62. Flexible piping 54 runs from vacuum connection 62 to tee 76 of vacuum connection 42.

Vacuum connection 42 is hermetically but removably sealed to upper nipple 78 on top 48. Flange 93 of duckbill check valve 90 having opening 92 is attached to inner bottom edge 91 of connection 42. Pour spout 58 is visible behind connection 42 and nipple 78.

Splash guard/float guide 84 is connected by three vertical ribs 85 (only one of which is shown) to lower nipple 79 on lid 48. Float valve 86 is free to move vertically within guard/guide 84. When liquid within liner 50 reaches a certain height, float valve 86 is raised by buoyant forces and the rounded top of valve 86 seat against valve seat 88 at the bottom of lower nipple 79.

When suction is drawn on the canister through tubing 40, air in the liner is withdrawn along the following vacuum path. The air in liner 50 passes up between guard/guide 84 and lower central rim 80 on lid 48. The air then flows downward, between guard/guide 84 and lower nipple 79. The air next turns upward around valve seat 88 and passes up through the passageway of nipple 79, through opening 98, into duckbill valve 90, through valve opening 92, into vacuum connection 42, and finally into vacuum source tubing 40 to the source of vacuum.

Additionally, while vacuum is pulled on the inside of the liner through the first vacuum path just described, vacuum is also pulled on void space 74 through the second vacuum path: the air in void space 74 passes out through opening 72 in connection 62, through piping 54, through side opening 75 in tee 76, and into vacuum connection 42.

Reduced pressure in liner 50 causes fluid (liquid or liquid plus gas) to flow through tubing 34, through fluid connection 36, and into liner 50. Baffle 82 prevents entering liquid from being drawn between lower rim 80 and splash guard/float guide 84 into the hospital's vacuum system.

Because the pressure drop through the first vacuum path is greater than through the second vacuum path (due to the drop through the duckbill check valve), when the vacuum is initially applied through vacuum connection 42, the pressure inside liner 50 will be greater than in void space 74. Therefore, if a flexible liner is used, initial application of the vacuum will cause the liner to expand fully to the configuration shown in FIG. 5.

However, in contrast to devices such as that disclosed in U.S. Pat. No. 3,680,560, the liner of the present device remains fully expanded even if there is an operating upset (e.g., blockage of vacuum source tubing 40). That is because of the check valve employed herein.

If there is an upset the check valve prevents collapse of the liner by ensuring that the pressure in the liner under normal operating conditions and under most upset conditions will be greater than that in the void space (because of the drop through the valve). Additionally, if the void space or vacuum system pressure should become greater than that in the liner, the check valve prevents the reverse flow of air into the liner. (That feature also makes sterile collection of liquid possible.) Keeping the liner expanded is desirable because if the liner collapses, the walls of liner 50 are not in the proper spatial relationship with the walls of container 46, making accurate determination of the quantity of liquid collected in the liner using volumetric indicia 52 on container 46 (FIG. 2) difficult. Furthermore, collapse of the liner may lead to contamination of the hospital's vacuum system.

Figure 6:
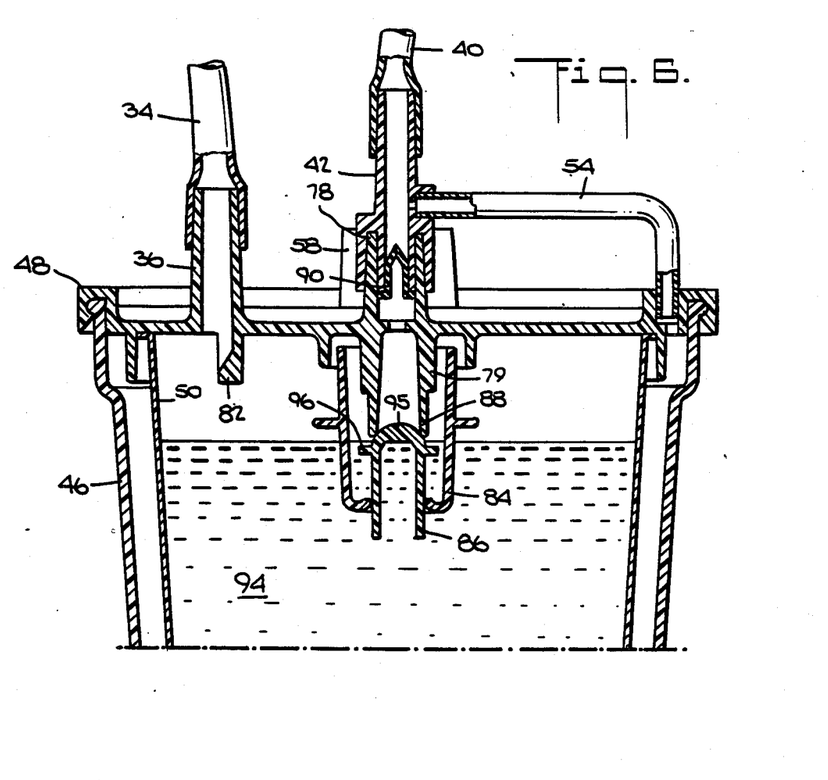
FIG. 6 is a detail view of FIG. 5 showing the float valve moved up by buoyant forces.

In FIG. 6 liquid 94, entering through liquid connection 36 under the urging of vacuum applied through vacuum connection 42, has reached a height sufficient to lift float valve 86 off its resting position on the inner lower rim of guard/guide 84 to seat against valve seat 88 of lower nipple 79. Rounded top 95 and shoulder 96 of valve 86 ensure that valve 86 seats properly to cut suction to the device. If the valve does not seat properly, suction to the liner is not halted and additional liquid drawn into the device may enter the hospital's vacuum system.

At this point tubing 34 and 40 are removed from fluid and vaccum connections 36 and 42, respectively, and lid 48 and liner 50 (filled with liquid) are removed as a unit, usually for disposal. Connection 42 is removed from upper nipple 78 and a cap (not shown) is placed on the nipple to prevent spillage during disposal. A new lid 48 with attached liner 50 is placed on container 46 and tubing 34 and 40 are reconnected. Since the flexible liner will usually be stored in collapsed form with its lid, the vacuum will initially expand the fresh liner, as explained above.

Figure 7:
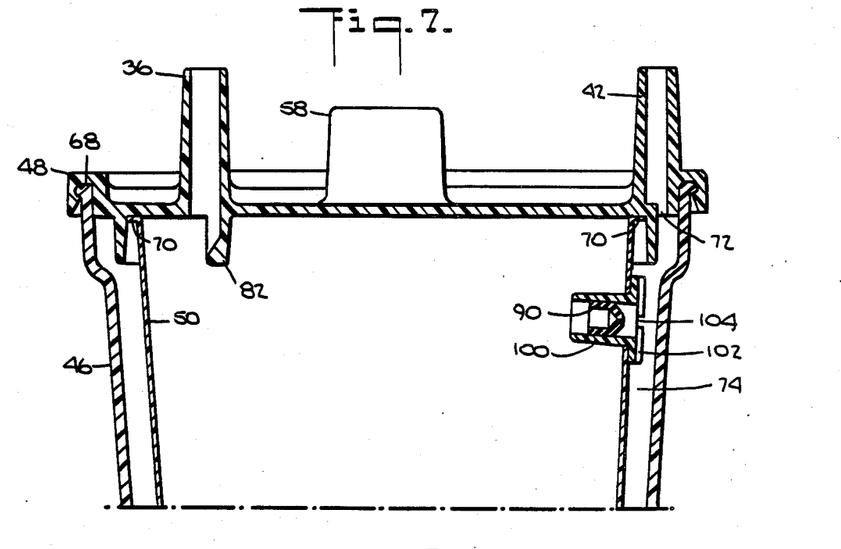
FIGS. 7 and 8 are enlarged detail views analogous to FIG. 6 of alternative embodiments.

FIG. 7 shows an alternative embodiment of the device wherein duckbill valve 90 is contained in nozzle 100, which is mounted in the sidewall of liner 50. Additionally, vacuum connection 42 has been moved to near the periphery of lid 48 so that it is over one section of void space 74. Liner 50 is heat-sealed at liner rim 70 to lid 48, which snap fits onto rim 68 of container 46. Pour spout 58 is fully visible.

When suction is drawn through vacuum connection 42, air in void space 74, between the wall of container 46 and liner 50, flows into connection 42 through opening 72. Additionally, air inside liner 50 passes out of the liner through duckbill check valve 90 in nozzle 100, through channels 104 in liner vacuum port 102, and into void space 74, from which the air is removed as described above. Fluid from the patient enters liner 50 through connection 36, as before.

Figure 8:
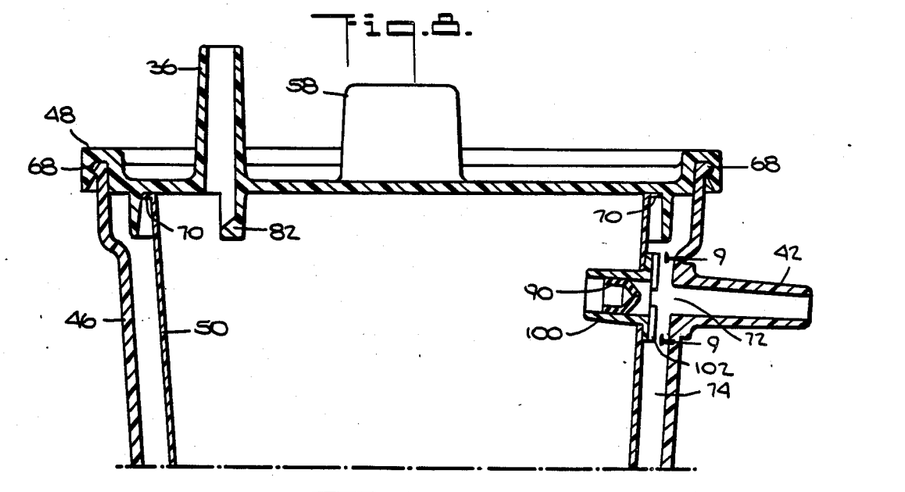

The device of FIG. 8 is the same as that of FIG. 7 except that vacuum connection 42 has been moved from top 48 to the sidewall of container 46. Air in void space 74 flows through opening 72 into connection 42 when vacuum is drawn through connection 42. As with the device of FIG. 7 air in liner 50 is drawn into the vacuum system (not shown) through duckbill valve 90 in nozzle 100.

Figure 9:
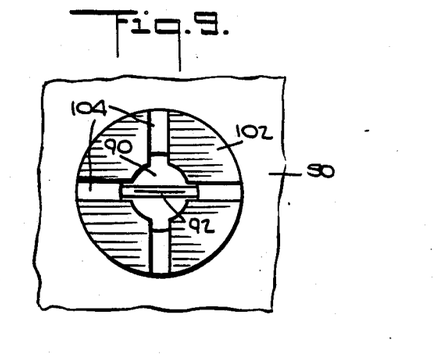
FIG. 9 is an enlarged sectional view taken along line 9—9 of FIG. 8.

FIG. 9 is an enlarged view of valve 90 and port 102 taken along line 9—9 of FIG. 8. Liner vacuum port 102 has two channels 104 along diameters of port 102. Air leaving the inside of liner 50 flows through opening 92 and then through channels 104 before passing into void space 74. Referring to FIGS. 7 and 8, nozzle 100 is attached to the sidewall of liner 50 so that air cannot pass out of the liner through the joint but only through valve 90. Preferably, the joint is made hermetic by heat-sealing port 101 to liner 50.

Figure 10:
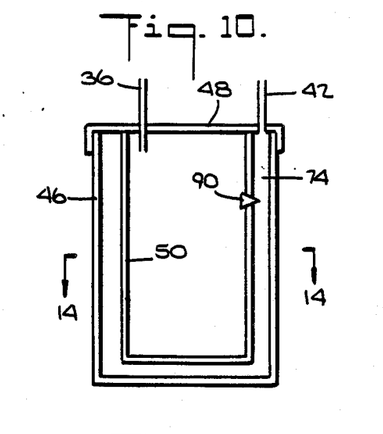
FIGS. 10 to 13 and 16 to 21 are schematic views of alternative embodiments of the canister of this invention.

FIGS. 10 to 21 schematically illustrate a number of alternative embodiments of the present invention. In these schematics, as before, reference numeral 36 denotes the fluid inlet connection; 42, the vacuum connection; 46, the container; 48, the top; 50, the liner; 54, vacuum piping; 74, the void space; and 90, the duckbill check valve. FIG. 10, for example, corresponds to FIG. 7.

Figure 11:
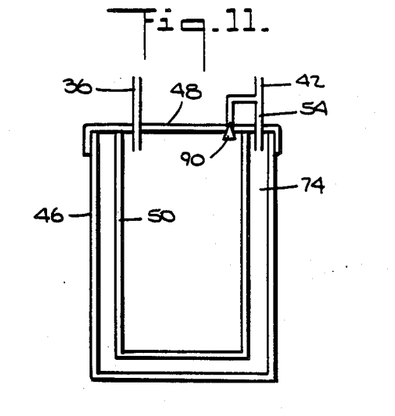

In FIG. 11 air leaving void space 74 flows through flexible piping 54 into vacuum connection 42. Air withdrawn from liner 50 through check valve 90 also flows into vacuum connection 42. Fluid from the patient enters liner 50 through fluid connection 36. The device of FIG. 12 is the same as that of FIG. 11 except that vacuum piping 54 is attached to the sidewall of container 46 rather than top 48.

Figure 13:
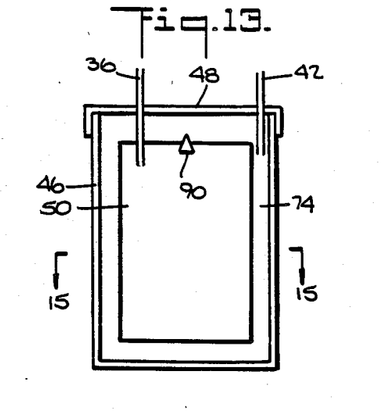

In FIG. 13 liner 50 is hermetically attached to and hangs from the portion of fluid connection 36 inside the device rather than being attached to the inside of top 48 as in the previous devices. Air in liner 50 is withdrawn through check valve 90, passes into void space 74, and leaves through vacuum connection 74.

Figures 12, 14:
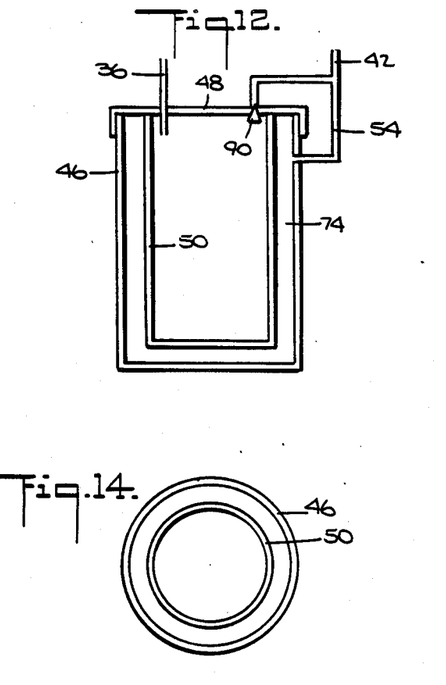
FIGS. 14 and 15 are cross-sectional views of two of the alternative embodiments of the suction canister, with FIG. 14 taken along line 14—14 of FIG. 10 and FIG. 15 taken along line 15—15 of FIG. 13.
Figure 15:
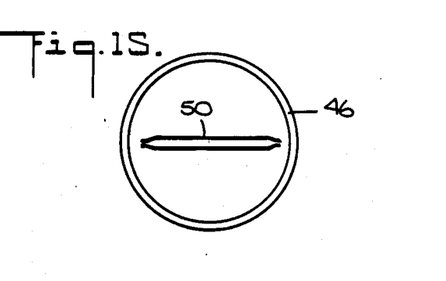

FIGS. 14 and 15 illustrate two of the many possible liner designs. In FIG. 14 the liner when expanded is cylindrical (FIG. 14 is a cross-sectional view taken along line 14—14 of FIG. 10). The liner of FIG. 15 is shown unexpanded; when expanded the cross-section will be approximately elliptical (FIG. 15 is a cross-sectional view taken along line 15—15 of FIG. 13).

Figure 16:
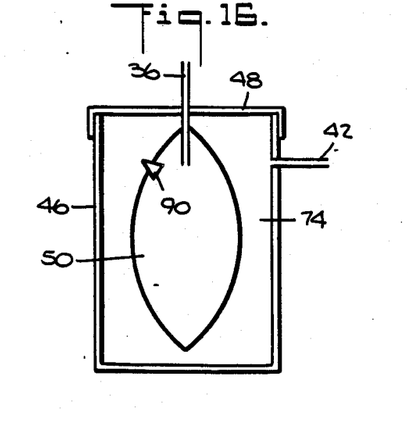

FIG. 16 shows an embodiment using a liner that is football-shaped. Vacuum connection 42 is in the sidewall of container 46 and air leaves liner 50 through check valve 90 and passes into void space 74 before leaving through connection 42.

Figure 17:
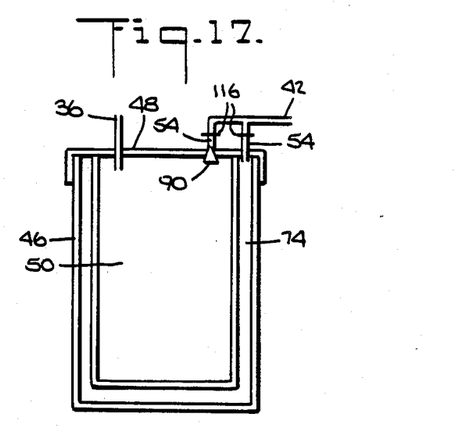

The device of FIG. 17 is the same as that of FIG. 11 except that conduit connectors 116 have been added to vacuum piping 54 leading to vacuum connection 42 from void space 74 and liner 50. Thus, both vacuum lines 54 may be disconnected at connectors 116 from vacuum connection 42. That makes fabrication of top 48 less complex and means that only two caps (not shown) are needed to seal fluid inside the liner when fluid collection has been completed (one cap on fluid connection 36 and the other on the vacuum piping 54 above check valve 90.

Another embodiment (not shown) is the same as that of FIG. 17 except that check valve 90 is between left connector 116 and vacuum connection 42 rather than being between left connector 116 and the inside of liner 50 as in FIG. 17.

Figure 18:
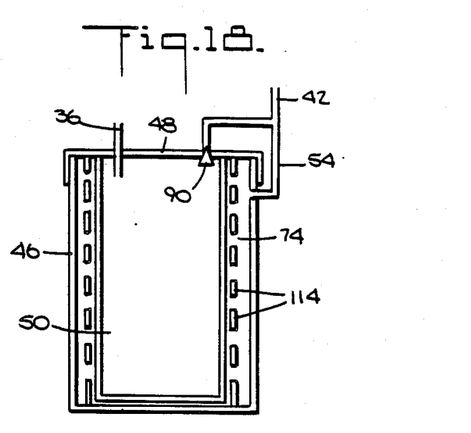

The embodiment of FIG. 18 is the same as that of FIG. 12 except that circumferential internal ribs 114 have been added to the inner sidewall of container 46. These ribs help support liner 50 and facilitate its removal when it is fully distended with liquid.

Figure 19:
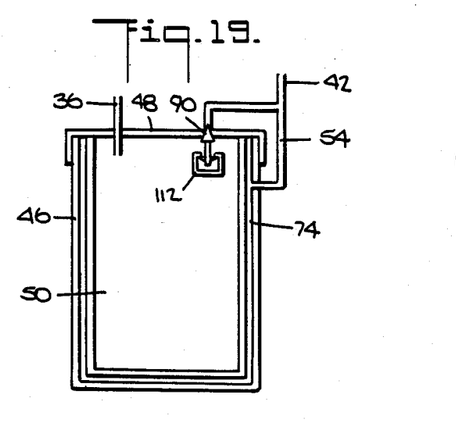

In the device of FIG. 19 float valve assembly 112 (analogous to valve 86, guard/guide 84, and seat 88 of FIG. 5) has been added. In all other respects the device is the same as that of FIG. 12. As explained above, the float valve is raised by buoyant forces when the liner fills with liquid to a predetermined level. The valve blocks the flow of any air out of the liner (halts suctioning) and that, in turn, halts the flow of liquid into the liner.

Figure 20:
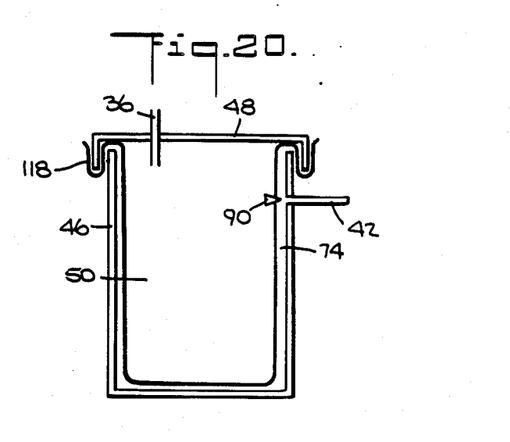
Figure 21:
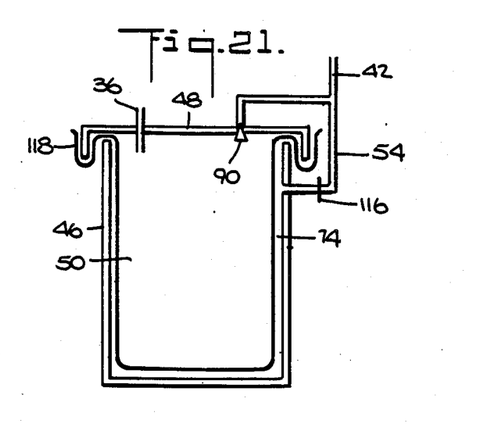

In FIGS. 20 and 21 liners 50 are not hermetically sealed to canister tops 48. Instead, upper circumferential portion 118 of each flexible liner is held tightly enough between its respective lid 48 and the upper edge of its respective container 46 to form a hermetic seal. In FIG. 20 when the liner is to be removed from its container 46, top 48 is unfastened (e.g., unsnapped or unscrewed) from the container, thereby freeing the portion of the liner trapped between the lid and the container. The upper circumferential portion 118 and liner 50 is grasped and pulled up and the trapped lid 48 and liner are removed from the container. In FIG. 21 to remove liner 50 and top 48 conduit connector 116 must first be opened.

Figure 22:
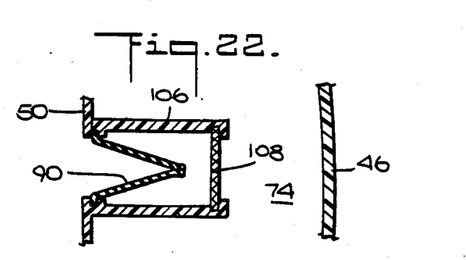
FIGS. 22 and 23 are alternative embodiments of duckbill check valve/membrane valve assemblies.
Figure 23:
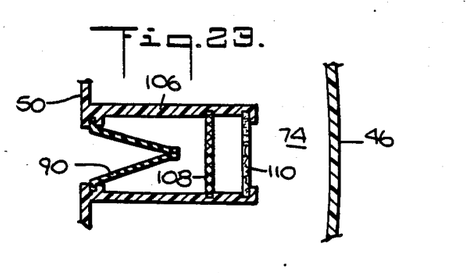

FIG. 22 shows another way of mounting check valve 90 in the wall of liner 50 as, for example, in the device of FIG. 20. Nozzle 106 is hermetically sealed to liner 50 so that during normal operation air can leave the liner only through check valve 90. Membrane valve 108 is air pervious/liquid impervious. Thus, air leaving check valve 90 under the force of suction can flow through membrane valve 108. But if liquid should reach nozzle 106 and flow through valve 90, membrane valve 1078 prevents that liquid from leaving nozzle 106 and passing into void space 74. Liquid entering void space 74 would contaminate container 74 and might rise to a high enough level in the container or splash so as to enter the hospital's vacuum system. To further safeguard the hospital's vacuum system from contamination, microbial air filter 110 may be added to nozzle 106, as in FIG. 23.

Figure 24:
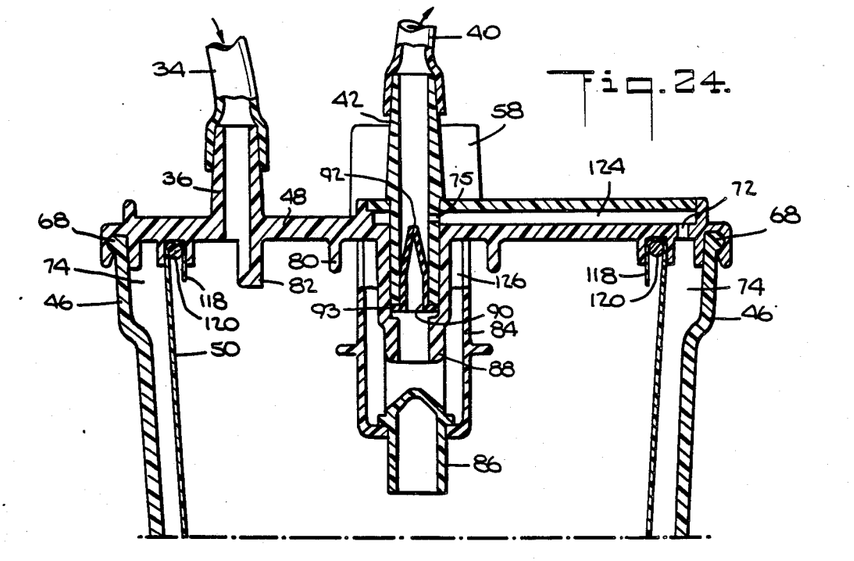
FIG. 24 is a sectional elevational view analogous to FIG. 5 of the preferred apparatus of the present invention.

FIG. 24 is a cross-sectional view (analogous to that of FIG. 6) of the most preferred embodiment of the present invention. In most respects the device is the same as that of FIGS. 1 to 6. Top 48 snaps onto rim 68 of container 46. Fluid from the patient flows through tubing 34 and fluid connection 36, past baffle 82, and into liner 50, which is hermetically sealed to top 48 by retaining ring 120.

Vacuum is drawn on the device through vacuum tubing 40, attached to vacuum connection 42. Flange 93 of duckbill valve 92 is hermetically sealed to the bottom of removable vacuum connection 42. When suction is drawn on the device, air in void space 74 flows through opening 72 into vacuum passageway 124 within top 48, through opening 75 in the side of vacuum connection 42, through the upper part of vacuum connection 42, and into vacuum tubing 40. At the same time, air in liner 50 flows into splash guard/float guide 84 through air passageways 126, around valve seat 88, through duckbill valve 90, and into vacuum connection 42. Float valve 86 closes off the inside of the liner from suction if the liquid level in liner 50 becomes too high, in the same way as shown in FIG. 6. When the liner is to be removed from the container, connection 42 is removed from the lid and a plug inserted therefor to prevent spillage.

Figure 25:
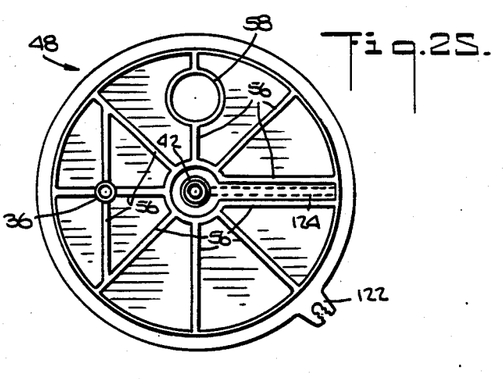
FIG. 25 is a top view of the preferred apparatus.

FIG. 25 is an overhead view of lid 48 of the device of FIG. 24. This top is similar to that of FIG. 4, the major difference being the addition of internal vacuum passageway 124. Also, retaining clip 122 for tubing has been added. The underside of that clip (analogous to tab 64 of FIG. 4) can be pushed upwardly to help remove lid 48 from container 46.

Figure 26:
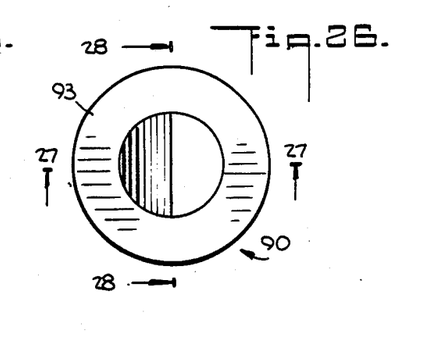
FIG. 26 is a top view of the preferred duckbill valve, used in the canister of FIG. 24.
Figure 27:
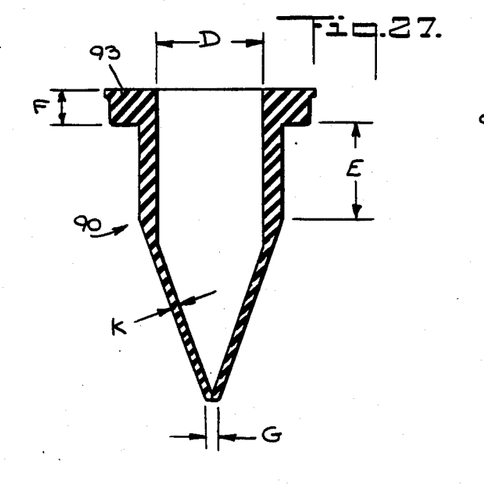
FIGS. 27 and 28 are sectional elevational views of the preferred duckbill check valve taken along lines 27—27 and 28—28 of FIG. 26, respectively.
Figure 28:
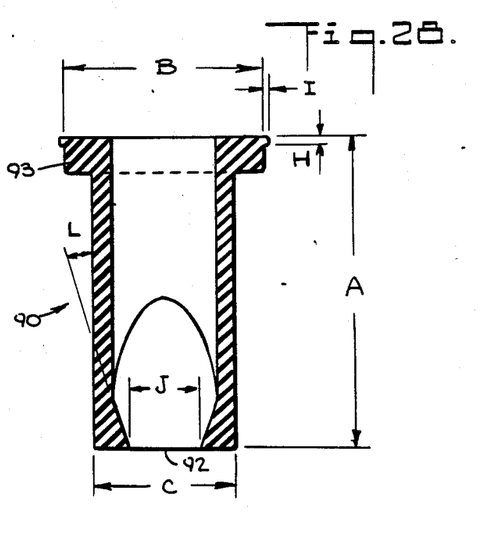

FIG. 26 is an overhead view of the preferred check valve of the present invention, a duckbill check valve. FIGS. 27 and 28 are cross-sectional views taken along lines 27—27 and 28—28, respectively, of FIG. 26. The preferred duckbill check valve used herein is designed to allow a flow of at least 90 SCFH (standard cubic feet per hour) of air when subject to a vacuum of 300 mm Hg (millimeters of mercury) with atmospheric pressure on the upstream (inlet) side and the valve has the following dimensions (approximately):

| Reference Letter | Dimension |
|---|---|
| A | 0.65–0.67 inches |
| B | 0.42–0.43 inches |
| C | 0.29–0.30 inches |
| D | 0.22–0.23 inches |
| E | 0.20–0.21 inches |
| F | 0.07–0.08 inches |
| G | 0.02–0.03 inches |
| H | 0.02 inches maximum |
| I | 0.01 inches maximum |
| J | 0.12–0.18 inches |
| K | 0.015 inches |
| L | 17 degrees |

Preferably, the duckbill check valve is molded from silicone rubber and slit 92 of length J is made after molding. Other elastomers may be used.

As will be obvious to one skilled in the art, numerous modifications and variations may be made and the claims are intended to cover all modifications and variations that fall within the true spirit and scope of the invention. For example, the liner and housing (container plus lid) may be made of any pharmacologically acceptable material. Polyvinylchloride (PVC) has been found to be suitable for the liner and polycarbonate for the housing. If a PVC liner is to be attached to the lid by heat sealing, the lid should also be of PVC. The vacuum connection may be on the lid of the sidewall of the container. The liner may be hermetically sealed to the lid or fluid connection in any suitable fashion. Heat-sealing or use of a pressure-fit retaining ring is preferred.

Suction may be drawn on the inside of the liner through the top or sidewall of the liner, but no matter how suction is drawn it must be through a check valve. Any type of check valve may be used but preferably a duckbill check valve is employed. Other types of check valves useful herein include flap, spring-loaded bill, and spring-loaded poppet. The check valve may be biased closed so that a preselected differential pressure is required to open it. That is especially useful if the liner is elastic (like a toy balloon). Without the biasing an elastic liner would quickly decrease in size if fluid flow from the patient into the liner were halted and liquid would be expelled from the liner (like gas rapidly escaping from a toy balloon), thereby possibly contaminating the vacuum system.

A float valve may be used to cut off suction when the liquid reaches a predetermined height. Membrane valves and microbial filters may also be used in the same nozzle as the check valve or in a separate part of the vacuum path. A second check valve allowing the flow of air out of the void space into the vacuum system but preventing the reverse flow may also be used. The second vacuum path containing the second check valve should have a lower pressure drop through it than the first vacuum path so that the liner will expand upon initial application of the vacuum.

I claim:

1. A medical suction canister for receiving fluid from a patient during a fluid suctioning procedure under the force of vacuum created by a vacuum source, said canister comprising:
   (a) a housing;
   (b) a flexible liner disposed within the housing, a void space being formed between the outside of the liner and the inside of the housing;
   (c) fluid path means for conducting fluid from the patient to the inside of the liner;
   (d) vacuum path means for applying suction (i) to the inside of the liner to cause fluid from the patient to flow into the liner and (ii) to the void space to remove gas therefrom; and
   (e) check valve means located in the vacuum path means (i) for expanding the flexible liner when suction is initially applied by the vacuum path means to the inside of the liner and to void space and (ii) for keeping the flexible liner expanded during the suctioning procedure, said check valve means oriented to permit gas to leave the inside of the liner and flow to the vacuum source and to block the reverse flow of gas from the vacuum source void space into the liner.

2. The medical suction canister of claim 1 wherein the check valve means is a duckbill check valve.

3. The medical suction canister of claim 2 wherein the duckbill check valve is of silicone rubber and can pass at least 90 SCFH of air when subjected to vacuum of 300 mm Hg.

4. The medical suction canister of claim 1 further comprising a removable top wherein the flexible liner is hermetically attached to the removable top.

5. The medical suction canister of claim 1 further comprising a float valve located in the vacuum path means to prevent liquid flow out of the flexible liner when the liquid level in the liner reaches a predetermined height.

6. A medical suction canister for receiving fluid from a patient during a fluid suctioning procedure under the force of vacuum created by a vacuum source, said canister comprising:
(a) a housing with a removable top;
(b) a flexible liner disposed within the housing hermetically attached to the removable top, a void space being formed between the outside of the liner and the inside of the housing;
(c) an inlet in the top for conducting fluid from the patient to the inside of the liner; and
(d) vacuum path and outlet means in the top for conducting gas from the inside of the liner and from the void space to the source of vacuum, said top having (i) a float valve to prevent liquid flow through the vacuum path and outlet means when the liquid level in the liner reaches a predetermined height and (ii) duckbill check valve means for expanding and keeping expanded the flexible liner when suction is applied through the vacuum path and outlet means to the inside of the liner and void space and for blocking the reverse flow of gas from the vacuum source or void space into the liner.

7. The medical suction canister of claim 6 wherein the duckbill check valve means is of silicone rubber and can pass at least 90 SCFH of air when subjected to a vacuum of 300 mm Hg.

* * * * *